United States Patent
Liu et al.

(10) Patent No.: US 11,727,609 B2
(45) Date of Patent: Aug. 15, 2023

(54) LIMITED-ANGLE CT RECONSTRUCTION METHOD BASED ON ANISOTROPIC TOTAL VARIATION

(71) Applicant: ZHEJIANG UNIVERSITY, Hangzhou (CN)

(72) Inventors: Huafeng Liu, Hangzhou (CN); Ting Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 395 days.

(21) Appl. No.: 16/979,168

(22) PCT Filed: Nov. 20, 2019

(86) PCT No.: PCT/CN2019/126882
§ 371 (c)(1),
(2) Date: Sep. 8, 2020

(87) PCT Pub. No.: WO2020/151424
PCT Pub. Date: Jul. 30, 2020

(65) Prior Publication Data
US 2020/0402274 A1    Dec. 24, 2020

(30) Foreign Application Priority Data
Jan. 24, 2019 (CN) .......................... 201910069082.8

(51) Int. Cl.
*G06T 11/00* (2006.01)
*A61B 6/03* (2006.01)
*A61B 6/00* (2006.01)

(52) U.S. Cl.
CPC ............ *G06T 11/006* (2013.01); *A61B 6/032* (2013.01); *A61B 6/5205* (2013.01); *G06T 11/005* (2013.01); *G06T 2210/41* (2013.01); *G06T 2211/436* (2013.01)

(58) Field of Classification Search
CPC . G06T 11/006; G06T 11/005; G06T 2210/41; G06T 2211/436; G06T 2211/424; A61B 6/032; A61B 6/5205; A61B 6/5258
See application file for complete search history.

(56) References Cited

U.S. PATENT DOCUMENTS

2016/0063694 A1* 3/2016 Shi .................. G06T 11/006
382/131

FOREIGN PATENT DOCUMENTS

| CN | 106846427 | 6/2017 |
| CN | 108280859 | 7/2018 |

* cited by examiner

*Primary Examiner* — Courtney D Thomas
(74) *Attorney, Agent, or Firm* — Jiwen Chen; Joywin IP Law PLLC

(57) ABSTRACT

The invention discloses a limited-angle CT reconstruction method based on Anisotropic Total Variation. According to the method, through an image reconstruction model using low dose and sparse-view-angle CT images, a fast iterative reconstruction algorithm is combined with an Anisotropic Total Variation method. The problems that in an existing limited-angle CT reconstruction method are effectively solved, such as partial boundary ambiguity, slow convergence speed and unable to accurately solve. In the process of solving the model, the slope filter is introduced in the Filtered Back-Projection to preprocess the iterative equation, and the Alternating Projection Proximal is used to solve the iterative equation, and the iteration is repeated until the termination condition is satisfied; the experimental comparison with the existing reconstruction methods shows that the invention can achieve better reconstruction effect.

5 Claims, 4 Drawing Sheets

(a)            (b)

LIMITED-ANGLE CT RECONSTRUCTION METHOD BASED ON ANISOTROPIC TOTAL VARIATION

This is a U.S. national stage application of PCT Application No. PCT/CN2019/126882 under 35 U.S.C. 371, filed Dec. 20, 2019 in Chinese, claiming priority of Chinese Application No. 201910069082.8, filed Jan. 24, 2019, all of which is hereby incorporated by reference.

TECHNICAL FIELD

The present invention belongs to the technical field of CT imaging, and particularly relates to a limited-angle CT reconstruction method based on Anisotropic Total Variation.

DESCRIPTION OF RELATED ART

X-ray CT has very important applications in many fields, such as the medical imaging field of diagnosis and treatment, the field of safety inspection, and the field of product quality inspection and control. In addition to conventional image reconstruction such as low dose CT reconstruction and sparse-angle CT reconstruction, the problem of limited angle has also been widely concerned. In the medical field, for the sake of patients' health, it is hoped that the X-ray exposure to the patients can be reduced as much as possible. At the same time, it is difficult for patients to remain immobile with X-ray exposure, it is hoped that the scan time can be shortened as much as possible. On the one hand, it can be achieved by reducing the X-ray dose, on the other hand, it can be achieved by reducing the X-ray irradiation time, including obtaining projection data for reconstruction with a sparser viewing angle or limiting the size of the projection viewing angle. In addition, there are some practical occasions where the scanning angle is limited. For example, when an X-ray microscope is used to image a biological sample, it will be restricted by the sample holder and cannot be imaged at full angle, or for some safety checks, it is impossible to image objects at full angle due to equipment limitations. Limited-angle CT reconstruction is a serious pathological problem, because the angle range of the projection data is smaller than the theoretical requirement of accurate reconstruction. In order to better solve this problem, some prior information is often used as the constraint of the problem, such as the non-negativity of the image, contour or boundary information, the sparsity of the image, etc.

For most natural images, especially medical images, fast-changing areas only exist at the boundaries of some structures, and most areas of the image are locally smooth, so even if an image itself is not sparse, its gradient image is likely to be sparse. Total Variation (TV) minimization takes advantage of this sparse nature of the image and is often used in the field of CT image reconstruction. The TV of an image is the L1 norm of its gradient image, which is minimized to be used as a constraint on the data fidelity term obtained by CT projection. This method can obtain better reconstruction results, less artifacts, and better recovery of boundaries.

Since we are studying the problem of limited-angle CT reconstruction, in addition to the prior information of image sparsity, there is another prior information that can be used, namely the angle range information. In 1988, Quinto theoretically analyzed the characteristics of the image reconstructed from the limited angle projection data and provided a conclusion: the boundary and details of the direction tangential to the projection direction are easier to be recovered, while images in other specific angles will have some artifacts and blur. The TV minimization method cannot detect blurry boundaries at certain angles during image reconstruction. In addition, since TV is the isotropic sum of the gradient magnitudes of all pixels in an image, it also includes the contribution of those fuzzy boundaries, so the ability to preserve edges for unambiguous boundaries will also decrease. Therefore, the concept of Anisotropic Total Variation (ATV) was proposed a few years ago. In addition to the sparsity of the image, the angle range of the projection data is used as another prior information to help reconstruction. The main idea of this method is to reduce the influence of the blurred boundary information on the boundary detection as much as possible, so that a better reconstructed image can be obtained.

There are many image reconstruction algorithms, usually based on some classic iterative algorithms such as Gradient Descent (GD), Algebraic Reconstruction Technique (ART), Simultaneous Iterative Reconstruction Technique (SIRT), Simultaneous Algebraic Reconstruction Technique (SART), and other improvements. These image reconstruction algorithms often combined with Ordered-Subsets Technique (OS) to accelerate. Most of these algorithms mainly have two problems: one is that the accuracy is not high when reconstructing the image from the projection data, and the other is that the slow convergence speed which causes a long time for reconstruction. Kudo et al. proposed a fast iterative reconstruction algorithm in 2016 to solve low dose CT and sparse angle CT reconstruction problems. This method used minimal data fidelity terms to perform iterative reconstruction, and used TV penalty terms to solve this problem. The process was constrained, and the solution was as follows: First, by using the Lagrangian dual method, the initial minimization problem was converted into a saddle point (original-dual) problem, and then the alternating projection in the first-order original-dual method was used to Alternating Projection Proximal (APP) to solve it; because the overall structure of this method is the same as the simultaneous iterative reconstruction algorithm such as SIRT and SART algorithm, the convergence speed was very slow, so the slope filter of Filtered Back-Projection (FBP) Rebuild was introduced to preprocess the iterative equation. This processing method does not affect the final iteration result. Its value is exactly the same as the solution of the original problem. The final algorithm can be understood as the slope filter is used to achieve the purpose of using FBP-type preprocessing to accelerate the first-order primal-dual method.

SUMMARY OF THE INVENTION

In view of the above, the present invention provides a limited-angle CT reconstruction method based on Anisotropic Total Variation. The method can solve the problem of partial boundary ambiguity existing in the existing CT reconstruction algorithm, improve the quality of CT image reconstruction, and accurately solve the objective equation with a fast convergence speed.

A limited-angle CT reconstruction method based on Anisotropic Total Variation, comprising the following steps:

(1) Using a detector to collect projection data of CT images in different angle directions to form a projection data set $\vec{b}$, wherein the projection data set $\vec{b}$ is composed of projection data vectors corresponding to each angle direction, the dimension of the projection data vectors is n, and the value of each element is the projection data measured by the corresponding detector, and n is the number of detectors;

(2) Establishing CT image reconstruction equations in a low dose mode and a sparse view mode respectively;

the expression of CT image reconstruction equation in a low dose mode is:

$$\min_{\vec{x}}\left(\beta\|\vec{x}\|_{ATV} + \frac{1}{2}\|A\vec{x}-\vec{b}\|^2\right), \text{ s.t. } \vec{x} \geq 0 \quad (1.1)$$

the expression of CT image reconstruction equation in a sparse view mode is:

$$\min_{\vec{x}}\|\vec{x}\|_{ATV}, \text{ s.t. } A\vec{x}=\vec{b}, \vec{x} \geq 0 \quad (2.1)$$

Wherein, $\vec{x}$ is the CT image data set and the dimension is k, k is the total number of pixels of the CT image, the value of each element $\vec{x}$ is the X-ray absorption coefficient of the corresponding pixel in the CT image to be reconstructed, A is a system matrix, and β is a given weight, $\|\ \|_{ATV}$ indicates Anisotropic Total Variation;

(3) Pre-processing the CT image reconstruction equations in the low dose mode and the sparse view mode to obtain the corresponding objective function, the pre-processing process comprises introducing a variable $\vec{y}$ and a non-singular matrix P, and using Lagrange duality to convert the CT image reconstruction equations into a saddle point problem;

(4) According to the actual situation, selecting and optimizing the objective function under the corresponding mode to obtain the CT image.

The pre-processing process of the CT image reconstruction equation in the low dose mode in the step (3) is as follows:

First, introducing the variable $\vec{y}$, the CT image reconstruction equation in the low dose mode is rewritten to the following form:

$$\min_{\vec{x}}\left(\beta\|\vec{x}\|_{ATV} + \frac{1}{2}\|\vec{y}-\vec{b}\|^2\right), \text{ s.t. } A\vec{x}-\vec{y}=0, \vec{x} \geq 0 \quad (1.2)$$

Wherein, $\vec{y}$ indicates the forward projection data calculated from the CT image data set $\vec{x}$.

Then, introducing the non-singular matrix P, equation (1.2) is further rewritten to the following form:

$$\min_{\vec{x}}\left(\beta\|\vec{x}\|_{ATV} + \frac{1}{2}\|\vec{y}-\vec{b}\|^2\right), \text{ s.t. } P^{1/2}(A\vec{x}-\vec{y})=0, \vec{x} \geq 0 \quad (1.3)$$

The Lagrange equation corresponding to equation (1.3) is as follows:

$$L(\vec{x},\vec{y},\vec{\mu})=\beta\|\vec{x}\|_{ATV}+\frac{1}{2}\|\vec{y}-\vec{b}\|^2+\vec{\mu}^T P^{1/2}(A\vec{x}-\vec{y})$$

Wherein, $\vec{\mu}$ is the Lagrange multiplier vector, T indicates transposition;

Equation (1.3) is converted to the saddle point problem, the specific expression is as follows:

$$\max_{\vec{\mu}}\min_{\vec{x}\geq 0,\vec{y}} L(\vec{x},\vec{y},\vec{\mu}) = \beta\|\vec{x}\|_{ATV} + \frac{1}{2}\|\vec{y}-\vec{b}\|^2 + \vec{\mu}^T P^{1/2}(A\vec{x}-\vec{y}) \quad (1.4)$$

Finally, the equation (1.4) is minimized and the variable $\vec{y}$ is removed, and the corresponding objective function is obtained as follows:

$$\max_{\vec{\mu}}\min_{\vec{x}\geq 0} L(\vec{x},\vec{\mu}) = \beta\|\vec{x}\|_{ATV} - \frac{1}{2}\|(P^{1/2})^T\vec{\mu}\|^2 - \vec{\mu}^T P^{1/2}\vec{b} + (P^{1/2})^T\vec{\mu}\cdot A\vec{x} \quad (1.5)$$

Wherein, ● indicates inner product operation.

The pre-processing process of the CT image reconstruction equation in the sparse view mode in the step (3) is as follows:

First, introducing the variable $\vec{y}$, the CT image reconstruction equation in sparse view mode is rewritten to the following form:

$$\min_{\vec{x}}\|\vec{x}\|_{ATV} \text{ s.t. } P^{1/2}(A\vec{x}-\vec{b})=0 \quad (2.2)$$
$$\vec{x}\geq 0$$

The Lagrange equation corresponding to equation (2.2) is as follows:

$$L(\vec{x},\vec{\mu})=\beta\|\vec{x}\|_{ATV}+\vec{\mu}^T P^{1/2}(A\vec{x}-\vec{b})$$

Equation (1.3) is converted to the saddle point problem, and the corresponding objective function is obtained as follows:

$$\max_{\vec{\mu}}\min_{\vec{x}\geq 0} L(\vec{x},\vec{\mu}) = \beta\|\vec{x}\|_{ATV} + \vec{\mu}^T P^{1/2}(A\vec{x}-\vec{b}) \quad (2.3)$$

Wherein, $\vec{\mu}$ is the Lagrange multiplier vector, T indicates transposition, β is the given weight.

The calculation expression of the non-singular matrix P is as follows:

$$P = F^{-1}R(\omega)F$$

$$R(\omega) = \frac{|\omega|}{2m\tau+|\omega|}$$

The calculation expression of the non-singular matrix P is as follows:

$$P = F^{-1}R(\omega)F$$

$$R(\omega) = \frac{|\omega|}{2m\tau}$$

Wherein, F and $F^{-1}$ are one-dimensional Fourier transform operator and inverse Fourier transform operator respectively, ω is the frequency domain variable after the Fourier transform of the projection data vector collected under the corresponding angle direction, m is the number of angle directions, and τ is a given parameter.

In the step (4), an Alternating Projection Proximal is used to optimize and solve the objective function to reconstruct the CT image, the parameters involved in the alternating projection approach algorithm include a total number of iterations $N_{iter}$, a number of TV denoising iterations $N_{ATV}$, and a iteration termination threshold δ and ∈, a TV term weighting coefficient β, a parameter α, a parameter τ, a parameter σ, a ATV weighting factors $γ_h$ and $γ_v$; wherein, the total number of iterations $N_{iter}$ ranges from 1~50000, the number of TV denoising iterations $N_{ATV}$ ranges from 1~10000, the iteration termination threshold δ and E ranges from $10^{-10}$~1, the TV term weighting coefficient β ranges from $10^{-6}$~1, the parameter α ranges from 0.01~0.25, the parameter τ ranges from $10^{-3}$~$10^3$, the parameter σ ranges from $10^{-3}$~$10^3$, the ATV weighting factors $γ_h$ and $γ_v$ ranges from $10^{-6}$~1.

The CT image reconstruction method of the invention utilizes the image reconstruction model of low dose and sparse view CT, combines the fast iterative reconstruction algorithm with the Anisotropic Total Variation method. The CT image reconstruction method effectively solves the problems existing in the existing limited-angle CT reconstruction methods, such as partial boundary ambiguity, slow convergence speed and unable to accurately solve. In the process of solving the model, the slope filter is introduced in the Filtered Back-Projection to preprocess the iterative equation, and the Alternating Projection Proximal is used to solve the iterative equation, and the iteration is repeated until the termination condition is satisfied; the experimental comparison with the existing reconstruction methods shows that the invention can achieve better reconstruction effect.

DETAILED DESCRIPTION OF THE INVENTION

In order to describe the present invention more specifically, the technical solution of the present invention will be described in detail below with reference to the drawings and specific embodiments.

Figure 1:
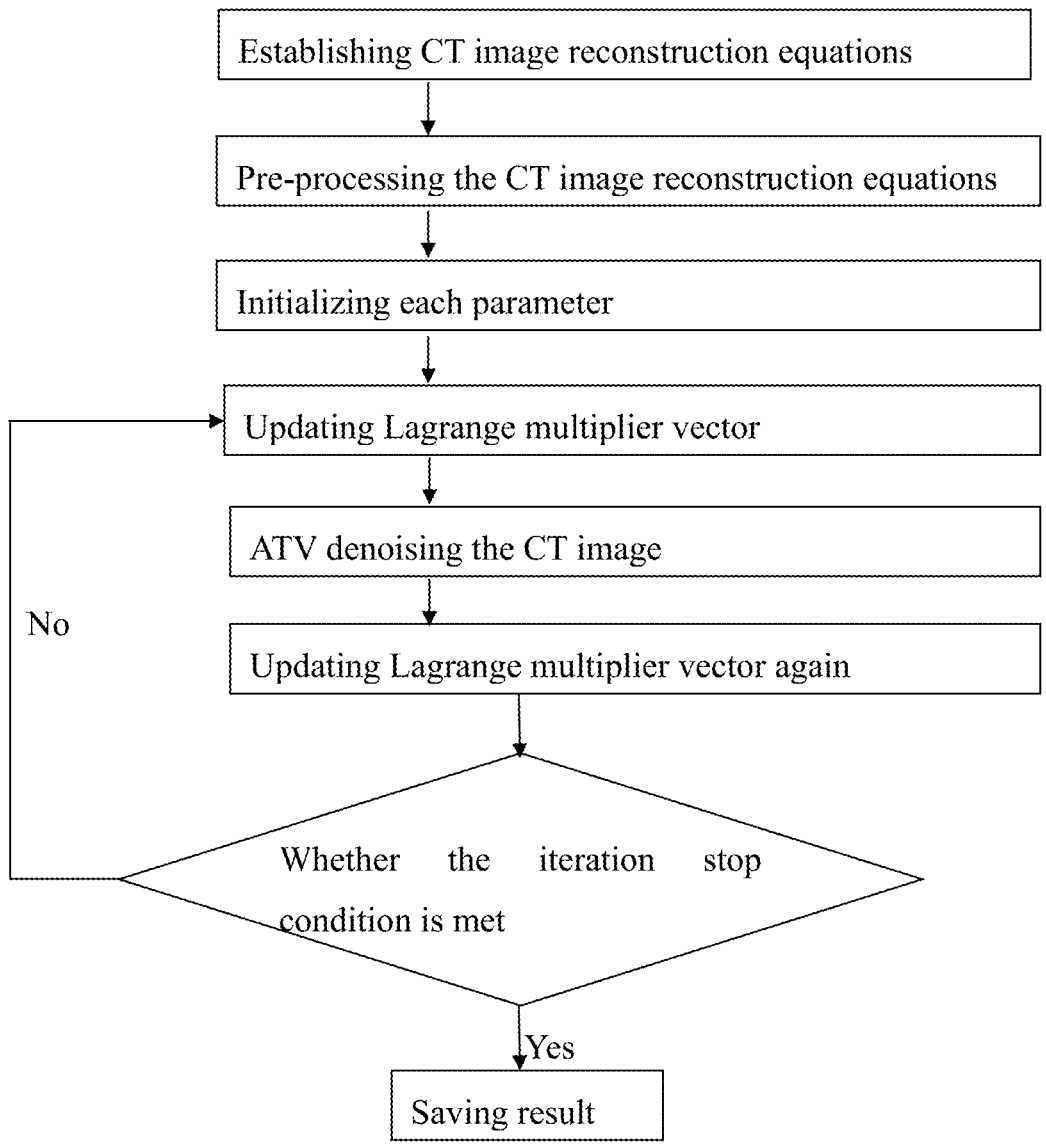
FIG. 1 is a schematic flowchart of a CT image reconstruction algorithm of the present invention.

As shown in FIG. 1, the limited-angle CT reconstruction method based on Anisotropic Total Variation of the present invention comprises the following steps:

(1) collecting CT images in different angle direction by using a detector to form a projection data set $\vec{b}$, the projection data set $\vec{b}$ is composed of projection data vectors corresponding to each angle directions, the dimension of the projection data vectors is n, and the value of each element is the projection data measured by the corresponding detector, and n is the number of detectors.

(2) Establishing CT image reconstruction equations in a low dose mode and a sparse view mode respectively:

The Low dose CT:

$$\min_{\vec{x}} \left( \beta \|\vec{x}\|_{ATV} + \frac{1}{2} \|A\vec{x} - \vec{b}\|^2 \right), \text{ s.t. } \vec{x} \geq 0 \quad (1)$$

The Sparse view CT:

$$\min_{\vec{x}} \|\vec{x}\|_{ATV}, \text{ s.t. } A\vec{x} = \vec{b}, \vec{x} \geq 0 \quad (2)$$

Wherein, $\vec{x}$ is the CT image data set and the dimension is k, k is the total number of pixels of the CT image, the value of each element $\vec{x}$ is the X-ray absorption coefficient of the corresponding pixel in the CT image to be reconstructed, A is the system matrix, A is suitable for various forms such as parallel beam projection, fan beam projection and cone beam projection, and β is a given weight, $\| \|_{ATV}$ indicates Anisotropic Total Variation.

In the case of a low dose CT, assuming that nm>k and $\vec{b}$ contains noise. In the case of a sparse view CT, assuming that nm<k and $\vec{b}$ does contain noise, m is the number of angle directions.

(3) Pre-processing the equation (1) and (2):

For the low dose CT, introducing the variable $\vec{y}$, the equation (1) is rewritten to the following form:

$$\min_{\vec{x}} \left( \beta \|\vec{x}\|_{ATV} + \frac{1}{2} \|\vec{y} - \vec{b}\|^2 \right), \text{ s.t. } A\vec{x} - \vec{y} = 0, \vec{x} \geq 0$$

Wherein, $\vec{y}$ indicates the forward projection data calculated from the CT image data set $\vec{x}$.

Introducing the non-singular matrix $P^{1/2}$, the above equation is rewritten to the following form:

$$\min_{\vec{x}} \left( \beta \|\vec{x}\|_{ATV} + \frac{1}{2} \|\vec{y} - \vec{b}\|^2 \right), \text{ s.t. } P^{1/2}(A\vec{x} - \vec{y}) = 0, \vec{x} \geq 0 \quad (3)$$

The Lagrange equation corresponding to equation (3) is as follows:

$$L(\vec{x}, \vec{y}, \vec{\mu}) = \beta \|\vec{x}\|_{ATV} + \frac{1}{2} \|\vec{y} - \vec{b}\|^2 + \vec{\mu}^T P^{1/2}(A\vec{x} - \vec{y})$$

Wherein, $\vec{\mu}$ is the Lagrange multiplier vector, equation (3) is converted to the saddle point problem:

$$\max_{\vec{\mu}} \min_{\vec{x} \geq 0, \vec{y}} L(\vec{x}, \vec{y}, \vec{\mu}) = \beta \|\vec{x}\|_{ATV} + \frac{1}{2} \|\vec{y} - \vec{b}\|^2 + \vec{\mu}^T P^{1/2}(A\vec{x} - \vec{y}).$$

The variable $\vec{y}$ can be removed by minimizing the above equation, and the corresponding objective function is obtained as follows:

$$\max_{\vec{\mu}} \min_{\vec{x} \geq 0} L(\vec{x}, \vec{\mu}) = \quad (4)$$

$$\beta \|\vec{x}\|_{ATV} - \frac{1}{2} \|(P^{1/2})^T \vec{\mu}\|^2 - \vec{\mu}^T P^{1/2} \vec{b} + (P^{1/2})^T \vec{\mu} \cdot A\vec{x}$$

$$P = F^{-1} R(\omega) F$$

$$R(\omega) = \frac{|\omega|}{2m\tau + |\omega|}$$

Wherein, ● indicates inner product operation, F and $F^{-1}$ are one-dimensional Fourier transform operator and inverse Fourier transform operator respectively, ω is the frequency domain variable after the Fourier transform of the projection data vector collected under the corresponding angle direction.

For sparse view CT, introducing the non-singular matrix $P^{1/2}$, the equation (2) is rewritten to the following form:

$$\min_{\vec{x}} \|\vec{x}\|_{ATV}, \text{ s.t. } P^{1/2}(A\vec{x} - \vec{y}) = 0, \vec{x} \geq 0 \quad (5)$$

The Lagrange equation corresponding to equation (5) is as follows:

$$L(\vec{x}, \vec{\mu}) = \beta \|\vec{x}\|_{ATV} + \vec{\mu}^T P^{1/2}(A\vec{x} - \vec{b})$$

The equation (5) is converted to the following form:

$$\max_{\vec{\mu}} \min_{\vec{x} \geq 0} L(\vec{x}, \vec{\mu}) = \beta \|\vec{x}\|_{ATV} + \vec{\mu}^T P^{1/2}(A\vec{x} - b) \quad (6)$$

$$P = F^{-1} R(\omega) F$$

$$R(\omega) = \frac{|\omega|}{2m\tau}$$

(4) Using an alternating projection approach algorithm to solve the equation (4) and (6):

4-1 Initializing $\vec{x} = 0$, $\vec{\mu} = 0$, and setting the value of each parameter: total number of iterations $N_{iter}$, the number of TV denoising iterations $N_{ATV}$, the iteration termination threshold $\delta$ and $\in$, the TV term weighting coefficient $\beta$, the parameter $\alpha$, the parameter $\tau$, the parameter $\sigma$, and the ATV weighting factors $\gamma_h$ and $\gamma_v$; wherein, the total number of iterations $N_{iter}$ ranges from 1~50000, the number of TV denoising iterations $N_{ATV}$ ranges from 1~10000, the iteration termination threshold $\delta$ and $\in$ ranges from $10^{-10}$~1, the TV term weighting coefficient $\beta$ ranges from $10^{-6}$~1, the parameter $\alpha$ ranges from 0.01~0.25, the parameter $\tau$ ranges from $10^{-3}$~$10^3$, the parameter $\sigma$ ranges from $10^{-3}$~$10^3$, the ATV weighting factors $\gamma_h$ and $\gamma_v$ ranges from $10^{-6}$~1.

4-2 The iteration count k=1 is setted initially.

4-3 Updating $\vec{\mu}$, when k is 1:

$$\vec{\mu}^{(k+1)} = -\sigma P \vec{b}$$

When k is not 1:

The Low dose CT: $\vec{\mu}^{(k+1)} = 2\vec{\mu}^{(k)} - \vec{\mu}^{(k-1)} - \sigma P(\vec{\mu}^{(k)} - \vec{\mu}^{(k-1)})$ The Sparse view CT: $\vec{\mu}^{(k+1)} = 2\vec{\mu}^{(k)} - \vec{\mu}^{(k-1)}$ 4-4 Updating $\vec{x}$:

$$\vec{x}^{(k+1)} = \arg\min_{\vec{x} \geq 0} \left( \tau\beta \|\vec{x}\|_{ATV} + \frac{1}{2} \|\vec{x} - (\vec{x}^{(k)} - \tau A^T \vec{\mu}^{(k+1)})\|^2 \right) \quad (7)$$

The equation (7) can be solved using the TV denoising algorithm of Chamball, $\vec{x}^{(k)} - \tau A^T \vec{\mu}^{(k+1)}$ is constant in this step, $\vec{z} = \vec{x}^{(k)} - \tau A^T \vec{\mu}^{(k+1)}$ is introduced for convenience, then the solving equation of equation (7) is:

$$p_{s,t}^{(k+1)} = \frac{p_{s,t}^{(k)} + \alpha(\nabla(div\vec{p}^{(k)} - \vec{z}/(\tau\beta)))_{s,t}}{1 + \alpha|(\nabla(div\vec{p}^{(k)} - \vec{z}/(\tau\beta)))_{s,t}|} \quad (8)$$

$$\vec{x}^{(k+1)} = \vec{z} - \tau\beta div\vec{p}^{(k+1)} \quad (9)$$

Wherein, $\nabla$ is a gradient operator, assuming that the size of the reconstructed image is N×N pixels. In this embodiment, it is defined as follows:

$$(\nabla \vec{x})_{s,t} = ((\nabla \vec{x})_{s,t}^1, (\nabla \vec{x})_{s,t}^2)$$

$$(\nabla \vec{x})_{s,t}^1 = \begin{cases} (x_{s+1,t} - x_{s,t})\gamma_h, & \text{if } s < N \\ 0, & \text{if } s = N \end{cases}$$

$$(\nabla \vec{x})_{s,t}^2 = \begin{cases} (x_{s+1,t} - x_{s,t})\gamma_v, & \text{if } t < N \\ 0, & \text{if } t = N \end{cases}$$

Then the Anisotropic Total Variation sub-item $\|\vec{x}\|_{ATV}$ is calculated as follows:

$$\|\vec{x}\|_{ATV} = \sum_{1 \leq s, t \leq N} |(\nabla \vec{x})_{s,t}|$$

For each $p_{s,t} = (p_{s,t}^1, p_{s,t}^2)$, the div operator is calculated as follows:

$$(div\vec{p})_{s,t} = \begin{cases} p^1_{s,t} - p^1_{s-1,t}, & \text{if } 1 < s < N \\ p^1_{s,t}, & \text{if } s = 1 \\ -p^1_{s-1,t}, & \text{if } s = N \end{cases} + \begin{cases} p^1_{s,t} - p^1_{s,t-1}, & \text{if } 1 < t < N \\ p^1_{s,t}, & \text{if } t = 1 \\ -p^1_{s,t-1}, & \text{if } t = N \end{cases}$$

Calculating $\in_c = (\|\vec{x}^{(k+1)}\|_{ATV} - \|\vec{x}^{(k)}\|_{ATV})/\|\vec{x}^{(k)}\|_{ATV}$, if $\in_c > \in$ and the number of repetitions does not reach $N_{ATV}$, the equation (8) and (9) is repeatedly calculated.

4-5 Updating $\vec{x}$ again:

The Low dose CT: $\vec{\mu}^{(k+1)} = \vec{\mu}^{(k)} \sigma P(A\vec{x}^{(k+1)} - \vec{b} - \vec{\mu}^{(k)})$ The Sparse view CT: $\vec{\mu}^{(k+1)} = \vec{\mu}^{(k)} + \sigma P(A\vec{x}^{(k+1)} - \vec{b})$ 4-6 Determine whether the sum of squares of all pixel values of the difference image of the reconstructed image $\vec{x}^{(k+1)}$ and he reconstructed image $\vec{x}^{(k)}$ is less than the iteration termination threshold δ or whether k is greater than $N_{iter}$; if yes, execute the step (4-7); if not, let k=k+1, execute the step (4-3)~(4-5).

4-7 Terminating the iteration and getting the final reconstructed image

Figure 2:
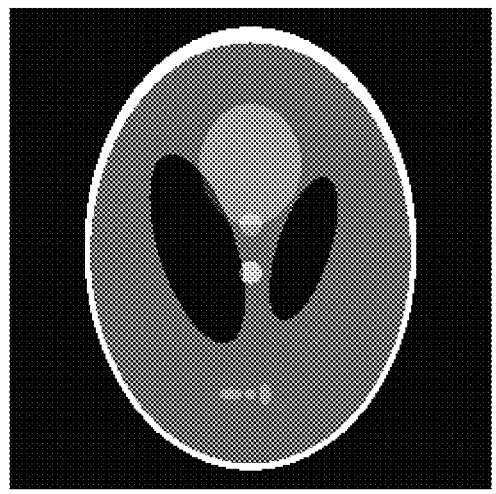
FIG. 2 shows the true value image of the Shepp & Logan phantom model, showing the gray range [1.00, 1.05].
Figure 3:
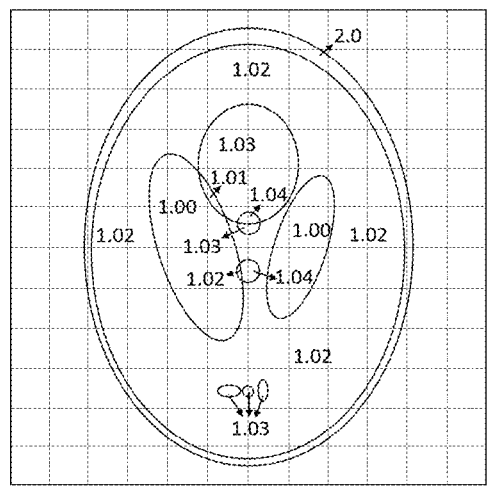
FIG. 3 shows the gray value image corresponding to the true value image of the Shepp & Logan phantom model.
Figure 4:
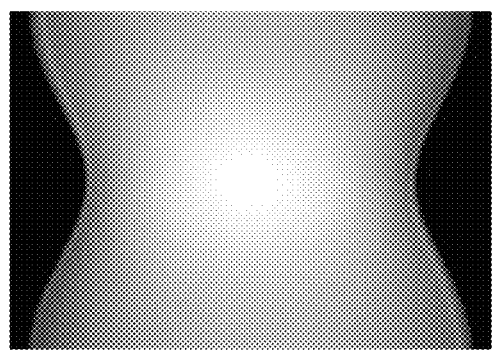
FIG. 4 shows the sonogram image (that is, a image composed of projection data at different angles, the angle range is 180°, and the angles is 180°) corresponding to the true value image of the Shepp & Logan phantom model.
Figure 5:
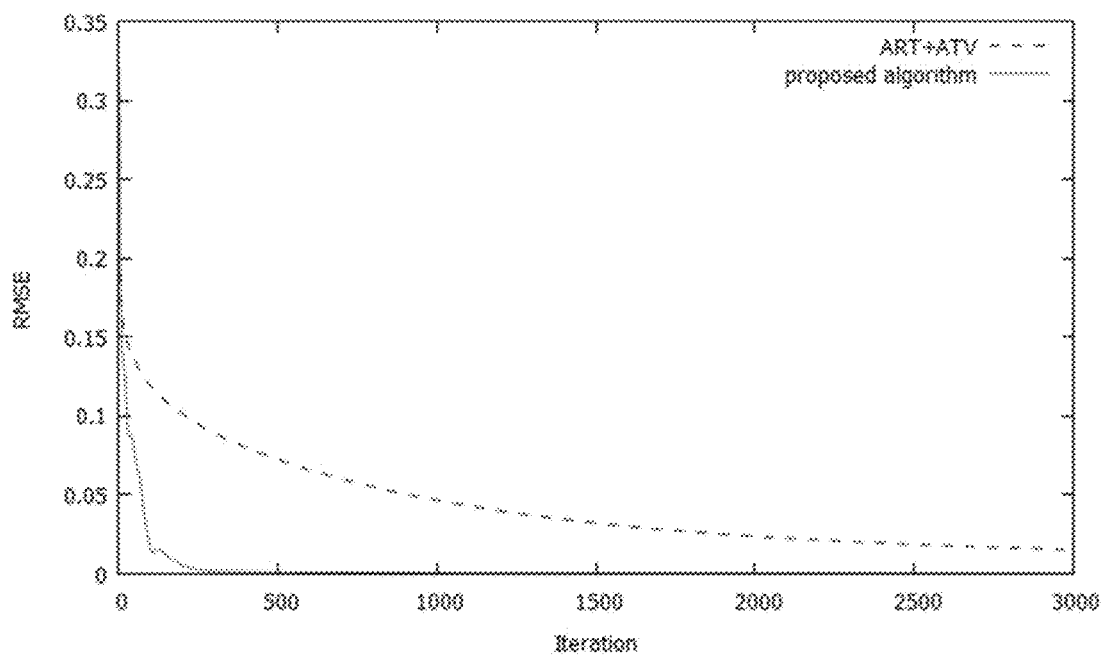
FIG. 5 shows the change of the root mean square error with the number of iterations of the reconstructed images obtained by the two methods (the method of the present invention and the Anisotropic Total Variation method) in the reconstruction process compared to the truth map, the angle range of the projection data is 120°, the angle is 120°.
Figure 6:
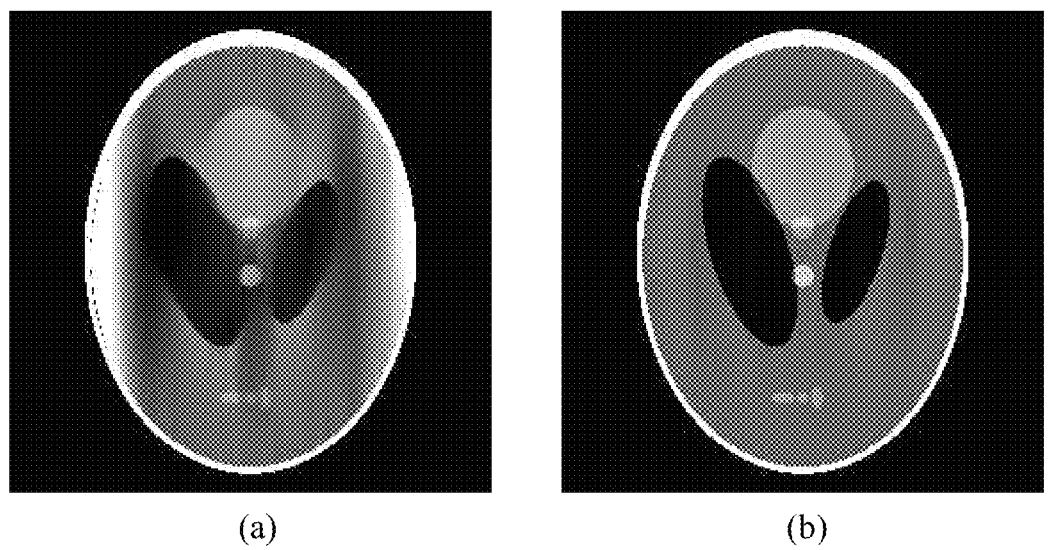
FIG. 6(a) shows the CT image reconstructed by the present invention by using the Shepp & Logan phantom model, the projection data angle range is 120% and the number of iterations is 3000 times.
FIG. 6(b) shows the CT image reconstructed by the Anisotropic Total Variation method by using the Shepp & Logan phantom model, the projection data angle range is 120% and the number of iterations is 3000 times.
Figure 7:
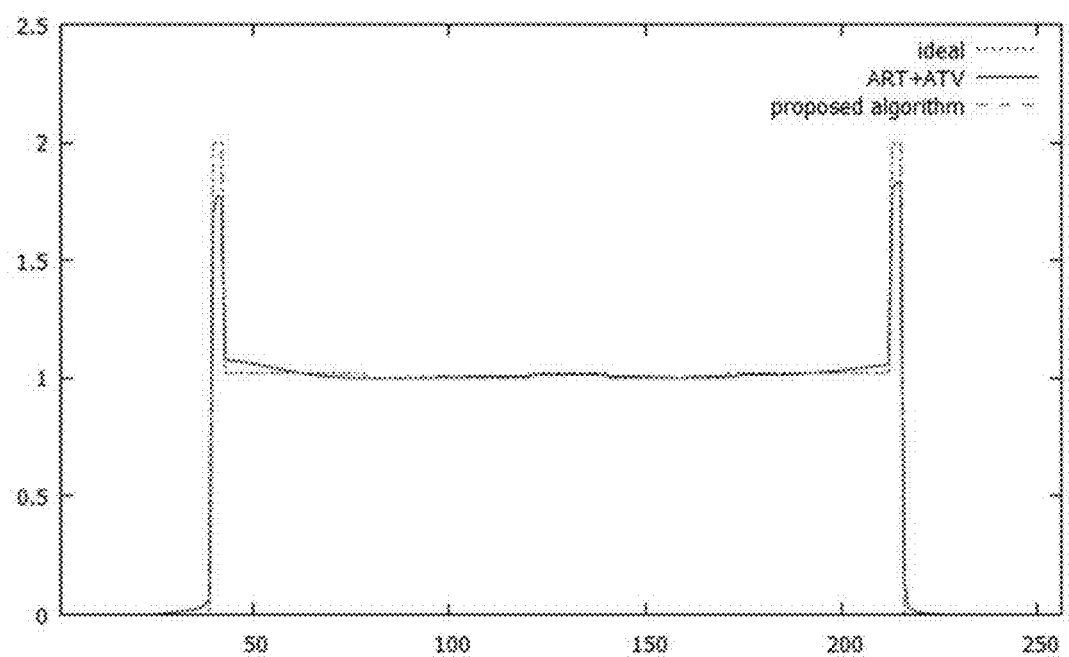
FIG. 7 is a schematic diagram comparing the horizontal midline of the reconstructed image and the true value of the reconstructed image obtained by the two methods (the method of the present invention and the Anisotropic Total Variation method), and the number of iterations is 3000 times.

The practicability and reliability of the implementation method by reconstructing the sinogram of the Shepp & Logan phantom mode are verified. The true value of the Shepp & Logan phantom mode is shown if FIG. 2 (due to the gray value of most of its structures is very close, in order to clearly display its structure, select the gray range [1.00, 1.05] for display), the corresponding gray value graph is shown in FIG. 3, and the sonogram (the angle range is 180°,) is shown in FIG. 4. The proposed method and the Anisotropic Total Variation method (ART+ATV) are used for reconstruction. FIG. 5 shows the change of the root mean square error with the number of iterations of the reconstructed images obtained by the two methods in the reconstruction process compared to the truth map. The FIG. 5 shows both methods gradually converge with the increase of the number of iterations, the root mean square error of the reconstruction result of the method of the present invention is smaller, and the convergence speed is very fast. The reconstructed image at the maximum number of iterations (that is, 3000 times) is selected and displayed. FIG. 6 (*a*) is the CT image reconstructed by the Anisotropic Total Variation method, and FIG. 6 (*b*) is the reconstructed image by the method of the present invention. It can be seen that the image artifacts reconstructed by the method of the present invention are much smaller, and the detailed information of the image can be better recovered, and the reconstruction effect is significantly better than the anisotropic full variation method. In order to more intuitively prove the superiority of the method of the present invention, FIG. 7 shows the comparison between the horizontal midline profile of the reconstructed image shown in FIGS. 6 (*a*) and 6 (*b*) and the true value profile. The section line of the method of the present invention almost completely coincides with the true value, that is, it can obtain a reconstruction result closer to the true value.

The above description of the embodiments is to facilitate those of ordinary skill in the art to understand and apply the present invention. Those skilled in the art can obviously make various modifications to the above-mentioned embodiments, and apply the general principles described here to other embodiments without creative work. Therefore, the present invention is not limited to the above-mentioned embodiments. According to the disclosure of the present invention, those skilled in the art should make improvements and modifications to the present invention within the protection scope of the present invention.

The invention claimed is:

1. A limited-angle computed tomography (CT) reconstruction method based on Anisotropic Total Variation, comprising the following steps:
    (1) using a detector to collect projection data of CT images of an object in different angle directions to form a projection data set $\vec{b}$, wherein the projection data set $\vec{b}$ is composed of projection data vectors corresponding to each angle direction, the dimension of the projection data vectors is n, and the value of each element is the projection data measured by the corresponding detector, and n is the number of detectors;
    (2) establishing CT image reconstruction equations in a low dose mode and a sparse view mode, respectively, by a processing circuit;
    the expression of CT image reconstruction equation in low dose mode being:

$$\min_{\vec{x}} \left( \beta \|\vec{x}\|_{ATV} + \frac{1}{2} \|A\vec{x} - \vec{b}\|^2 \right), \text{ s.t. } \vec{x} \geq 0 \quad (1.1)$$

the expression of CT image reconstruction equation in sparse view mode being:

$$\min_{\vec{x}} \|\vec{x}\|_{ATV}, \text{ s.t. } A\vec{x} = \vec{b}, \vec{x} \geq 0 \quad (2.1)$$

wherein, $\vec{x}$ is the CT image data set and the dimension is k, k is the total number of pixels of the CT image, the value of each element $\vec{x}$ is the X-ray absorption coefficient of the corresponding pixel in the CT image to be reconstructed, A is a system matrix, and β is a given weight $\| \|_{ATV}$ indicates Anisotropic Total Variation;
    (3) pre-processing the CT image reconstruction equations in the low dose mode and the sparse view mode by the processing circuit to obtain the corresponding objective function, the pre-processing process comprising introducing a variable and a non-singular matrix P, and using Lagrange duality to convert the CT image reconstruction equations into a saddle point problem;
    (4) according to the low dose image reconstruction mode or the sparse view image mode, selecting and optimizing the objective function under the corresponding mode to obtain the CT image, and outputting the CT image to an output display;
    wherein, in the step (4), an Alternating Projection Proximal is used to optimize and solve the objective function to reconstruct the CT image, the parameters involved in the alternating projection approach algorithm include a total number of iterations $N_{iter}$, a number of TV denoising iterations $N_{ATV}$, and a iteration termination threshold δ and $\in$, a TV term weighting coefficient β, a parameter α, a parameter τ, a parameter σ, an ATV weighting factors $\gamma_h$ and $\gamma_v$; wherein, the total number of iterations $N_{iter}$ ranges from 1~50000, the number of TV denoising iterations $N_{ATV}$ ranges from 1~10000, the iteration termination threshold δ and $\in$ ranges from $10^{-10}$~1, the TV term weighting coefficient β ranges from $10^{-6}$~1, the parameter α ranges from 0.01~0.25, the parameter $\tau$ ranges from $10^{-3}\sim10^3$, the parameter $\sigma$ ranges from $10^{-3}\sim10^3$, the ATV weighting factors $\gamma_h$ and $\gamma_v$ ranges from $10^{-6}\sim1$.

2. The limited-angle CT reconstruction method according to claim 1, wherein, the pre-processing process of the CT image reconstruction equation in the low dose mode in the step (3) is as follows:

$$\min_{\vec{x}}\left(\beta\|\vec{x}\|_{ATV}+\frac{1}{2}\|\vec{y}-\vec{b}\|^2\right),\ \text{s.t.}\ A\vec{x}-\vec{y}=0,\vec{x}\geq 0 \quad (1.2)$$

first, introducing the variable $\vec{y}$, the CT image reconstruction equation in the low dose mode is rewritten to the following form:

$$\min_{\vec{x}}\left(\beta\|\vec{x}\|_{ATV}+\frac{1}{2}\|\vec{y}-\vec{b}\|^2\right),\ \text{s.t.}\ A\vec{x}-\vec{y}=0,\vec{x}\geq 0 \quad (1.2)$$

wherein, $\vec{y}$ indicates the forward projection data calculated from the CT image data set $\vec{x}$;

then, introducing the non-singular matrix P, equation (1.2) being further rewritten to the following form:

$$\min_{\vec{x}}\left(\beta\|\vec{x}\|_{ATV}+\frac{1}{2}\|\vec{y}-\vec{b}\|^2\right),\ \text{s.t.}\ P^{1/2}(A\vec{x}-\vec{y})=0,\vec{x}\geq 0 \quad (1.3)$$

the Lagrange equation corresponding to equation (1.3) being as follows:

$$L(\vec{x},\vec{y},\vec{\mu})=\beta\|\vec{x}\|_{ATV}+\tfrac{1}{2}\|\vec{y}-\vec{b}\|^2+\vec{\mu}^T P^{1/2}(A\vec{x}-\vec{y})$$

wherein, $\vec{\mu}$ is the Lagrange multiplier vector, T indicates transposition;

$$\max_{\vec{\mu}}\min_{\vec{x}\geq 0,\vec{y}} L(\vec{x},\vec{y},\vec{\mu}) = \beta\|\vec{x}\|_{ATV}+\frac{1}{2}\|\vec{y}-\vec{b}\|^2+\vec{\mu}^T P^{1/2}(A\vec{x}-\vec{y}) \quad (1.4)$$

the equation (1.3) is converted to the saddle point problem, the specific expression is as follows:

$$\max_{\vec{\mu}}\min_{\vec{x}\geq 0,\vec{y}} L(\vec{x},\vec{y},\vec{\mu}) = \beta\|\vec{x}\|_{ATV}+\frac{1}{2}\|\vec{y}-\vec{b}\|^2+\vec{\mu}^T P^{1/2}(A\vec{x}-\vec{y}) \quad (1.4)$$

finally, minimizing the equation (1.4) and removing the variable $\vec{y}$, and the corresponding objective function being obtained as follows:

$$\max_{\vec{\mu}}\min_{\vec{x}\geq 0,\vec{y}} L(\vec{x},\vec{\mu}) = \quad (1.5)$$

$$\beta\|\vec{x}\|_{ATV}-\frac{1}{2}\|(P^{1/2})^T\vec{\mu}\|^2-\vec{\mu}^T P^{1/2}\vec{b}+(P^{1/2})^T\vec{\mu}\cdot A\vec{x}$$

wherein, ● indicates inner product operation.

3. The limited-angle CT reconstruction method according to claim 1, wherein, the pre-processing process of the CT image reconstruction equation in sparse view mode in the step (3) is as follows:

$$\min_{\vec{x}}\|x\|_{ATV}\ \text{s.t.}\ P^{1/2}(A\vec{x}-\vec{b})=0 \quad (2.2)$$
$$\vec{x}\geq 0$$

first, introducing the variable $\vec{y}$, the CT image reconstruction equation in sparse view mode being rewritten to the following form:

$$\min_{\vec{x}}\|x\|_{ATV}\ \text{s.t.}\ P^{1/2}(A\vec{x}-\vec{b})=0 \quad (2.2)$$
$$\vec{x}\geq 0$$

the Lagrange equation corresponding to equation (2.2) being as follows:

$$L(\vec{x},\vec{\mu})=\beta\|\vec{x}\|_{ATV}+\vec{\mu}^T P^{1/2}(A\vec{x}-\vec{b})$$

the equation (1.3) being converted to the saddle point problem, and the corresponding objective function being obtained as follows:

$$\max_{\vec{\mu}}\min_{\vec{x}\geq 0} L(\vec{x},\vec{\mu}) = \beta\|\vec{x}\|_{ATV}+\vec{\mu}^T P^{1/2}(A\vec{x}-\vec{b}) \quad (2.3)$$

wherein, $\vec{\mu}$ is the Lagrange multiplier vector, T indicates transposition, $\beta$ is the given weight.

4. The limited-angle CT reconstruction method according to claim 2, wherein, in the low dose mode, the calculation expression of the non-singular matrix P is as follows:

$$P = F^{-1}R(\omega)F$$

$$R(\omega) = \frac{|\omega|}{2m\tau+|\omega|}$$

wherein, F and $F^{-1}$ are one-dimensional Fourier transform operator and inverse Fourier transform operator respectively, $\omega$ is the frequency domain variable after the Fourier transform of the projection data vector collected under the corresponding angle direction, m is the number of angle directions, and $\tau$ is a given parameter.

5. The limited-angle CT reconstruction method according to claim 3, wherein, in the sparse view mode, the calculation expression of the non-singular matrix P is as follows:

$$P = F^{-1}R(\omega)F$$

$$R(\omega) = \frac{|\omega|}{2m\tau}$$

wherein, F and $F^{-1}$ are one-dimensional Fourier transform operator and inverse Fourier transform operator respectively, $\omega$ is the frequency domain variable after the Fourier transform of the projection data vector collected under the corresponding angle direction, m is the number of angle directions, and $\tau$ is a given parameter.

* * * * *